United States Patent [19]

Miller

[11] Patent Number: 4,467,086
[45] Date of Patent: Aug. 21, 1984

[54] CEPHALOSPORIN ANTIBIOTIC

[75] Inventor: Thomas Miller, Harefield, England

[73] Assignee: Glaxo Group Limited, London, England

[21] Appl. No.: 408,519

[22] Filed: Aug. 16, 1982

Related U.S. Application Data

[63] Continuation of Ser. No. 185,967, Sep. 9, 1980, abandoned.

[30] Foreign Application Priority Data

Oct. 2, 1979 [GB] United Kingdom ................. 7934203

[51] Int. Cl.³ .......................................... C07D 501/46
[52] U.S. Cl. ....................................... 544/25; 424/246
[58] Field of Search ........................... 544/25; 424/246

[56] References Cited

U.S. PATENT DOCUMENTS 4,258,041  3/1981  O'Callaghan et al. ............. 424/246

Primary Examiner—Paul M. Coughlan, Jr.
Attorney, Agent, or Firm—Bacon & Thomas

[57] ABSTRACT (6R,7R)-7-[(Z)-2-(2-Aminothiazol-4-yl)-2-(2-carboxyprop-2-oxyimino)acetamido]-3-(1-pyridiniummethyl) ceph-3-em-4-carboxylate in the form of a crystalline bishydrochloride.

The bishydrochloride has a well defined crystalline structure and exhibits good stability in storage. The bishydrochloride exhibits excellent antibiotic activity, particularly against organisms which are normally difficult to combat with β-lactam antibiotics.

1 Claim, 1 Drawing Figure

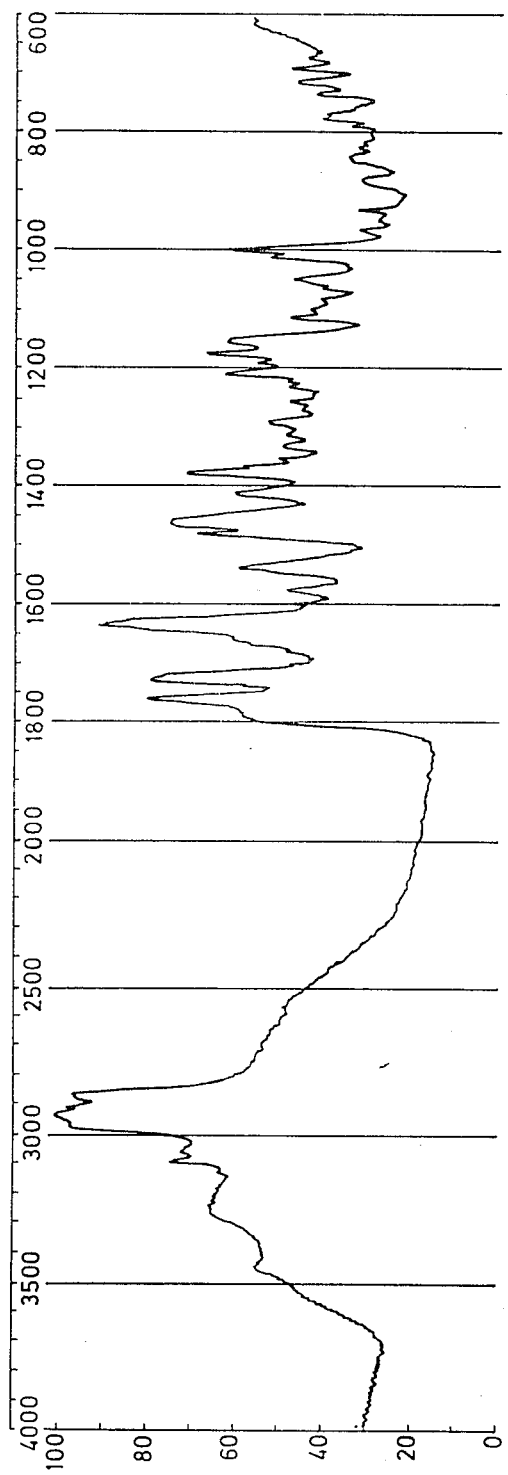

CEPHALOSPORIN ANTIBIOTIC

This application is a continuation of application Ser. No. 185,967, filed Sept. 9, 1980, now abandoned.

This invention relates to improvements in or relating to (6R,7R)-7-[(Z)-2-(2-aminothiazol-4-yl)-2-(2-carboxyprop-2-oxyimino)acetamido]-3-(1-pyridiniummethyl)-ceph-3-em-4-carboxylate of formula

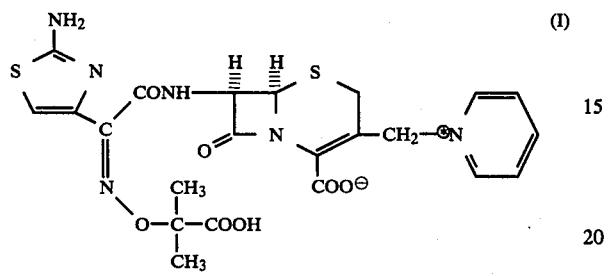

(I)

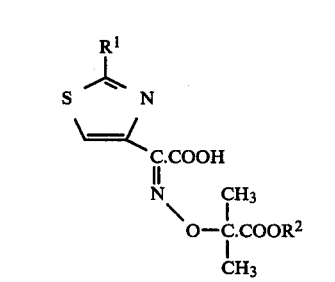

preferably as the bishydrochloride acid addition salt, with an acid of formula $$\begin{array}{c} R^1 \\ S \diagdown N \\ \| \quad \| \\ \diagup C.COOH \\ N \quad CH_3 \\ \diagdown O-\overset{|}{C}.COOR^2 \\ \overset{|}{CH_3} \end{array}$$

(wherein $R^1$ represents an amino or protected amino group; and $R^2$ represents a carboxyl blocking group) or with an acylating agent corresponding thereto; whereafter the following reactions may be carried out (i) removal of any amino-protecting group and the carboxyl blocking group $R^2$, and, if desired, (ii) conversion of a carboxyl group into a non-toxic salt.

The desired compound of formula (I) above and its bishydrochloride salt of UK Patent Specification No. 2025398 were obtained as amorphous solids and their stability was not particularly satisfactory, especially at elevated temperatures.

It has now been found that (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate (I) bishydrochloride can be advantageously prepared and isolated in crystalline form.

The crystalline form of the bishydrochloride compound is of generally superior quality in terms of its purity and stability. In particular, the new form of hydrochloride has been found to have a well-defined crystalline structure and it has been found to be remarkably stable even when stored for an extended period at a temperature of 50° C. These properties render it of value in pharmaceutical use as well as in the preparation of other active cephalosporin compounds.

It has been found that the new crystalline bishydrocholoride salt of the above cephalosporin compound can be prepared under controlled conditions. For example, it has been found that the desired crystalline bishydrochloride may be prepared by crystallisation from a suitable medium, for example comprising acetone and formic acid. It has also been found possible to recrystallise the crystalline bishydrochloride from a vareity of media. Examples of other media for crystallisation or recrystallisation include industrial methylated spirit and mixtures of methanol, n-propanol and diisopropyl ether.

Crystallisation of the dihydrochloride is preferably effected at a temperature of from 10° to 35° C., conveniently at about 20° C., followed by a step of cooling, to enhance crystal yield, to a temperature in the range from 0° to 15° C.

After precipitation, the crystalline bishydrochloride product may be recovered by filtration and washed and dried in conventional manner.

This compound, which is variously referred to as 'ceftazidime' and 'GR 20263', has been found to have broad spectrum antibiotic activity and, in particular, unusually high activity against gram-negative organisms, including many β-lactamase-producing gram-negative strains, as described in our UK Patent Specification No. 2025398. The compound possesses excellent activity against organisms normally difficult to combat with β-lactam antibiotics, such as indolepositive Proteus, Serratia, Providence and especially Pseudomonas organisms, and its antibacterial properties are not impaired by human serum. Moreover, the effect of increased inocula against the compound is low and the compound is rapidly bactericidal at concentrations close to the minimum inhibitory concentration. It is well distributed in the bodies of small rodents giving useful therapeutic levels after subcutaneous injection. Experimental infections in mice with gram-negative bacteria have been successfully treated using the compound and, in particular, excellent protection has been obtained against strains of *Pseudomonas aeruginosa*, an organism normally not susceptible to treatment with cephalosporin antibiotics. This protection was comparable with the treatment with an aminoglycoside such as amikacin. Acute toxicity tests with the compound in mice gave $LD_{50}$ values in excess of 6 g/kg. No nephrotoxicity has been observed in rats at dosages of 2.0 g/kg. In studies in human volunteers the compound has shown good pharmacokinetic properties, giving high and long lasting serum levels after injection. The long serum halflife suggests that less frequent dosages might be required for less serious infections. Early clinical results suggest that the compound reproduces in the clinic the excellent antibiotic properties demonstrated in vitro and in experimental animals.

UK Patent Specification No. 2025398 also discloses solvates and non-toxic salts, e.g. base salts and acid addition salts, of the above-mentioned cephalosporin compound.

UK Patent Specification No. 2025398 discloses, inter alia, a method for the preparation of the abovementioned cephalosporin compound (I) as well as solvates and non-toxic salts thereof, which comprises: acylating a compound of formula The bishydrochloride salt for use in the preparation of the new crystalline bishydrochloride according to the invention may be prepared by a process disclosed in the above-mentioned UK Patent Specification No. 2025398, i.e. by a process involving the method above-mentioned.

The new crystalline bishydrochloride according to the invention has been subjected to X-ray powder diffraction studies. The product of the following Example 2 was used to obtain a Debye Scherrer powder diffraction photograph by exposure for 12 hours to CoKα radiation and a second photograph by exposure for 3 hours to CuKα radiation. The line intensities were compared against a set of standards to give the relative intensities in the following Table:

TABLE

| 'd' value (Å) | Relative intensity $\left(\frac{I}{I_{100}}\right)$ | 'd' value (Å) | Relative intensity $\left(\frac{I}{I_{100}}\right)$ |
|---|---|---|---|
| 10.6 | 93 | 2.76 | 12 |
| 7.9 | 22 | 2.73 | 10 |
| 6.6 | 30 | 2.65 | 15 |
| 6.4 | 10 | 2.59 | 5 |
| 5.65 | 45 | 2.53 | 3 |
| 5.43 | 15 | 2.48 | 7 |
| 5.07 | 10 | 2.43 | 10 |
| 4.90 | 10 | 2.39 | trace |
| 4.70 | 12 | 2.35 | 7 |
| 4.54 | 10 | 2.26 | 10 |
| 4.25 | 100 | 2.24 | trace |
| 4.12 | 30 | 2.19 | 4 |
| 3.97 | 30 diffuse | 2.11 | 2 |
| 3.89 | 65 | 2.09 | 4 |
| 3.82 | 25 | 2.06 | 2 |
| 3.75 | 35 | 2.03 | 2 |
| 3.60 | 35 | 1.963 | 2 |
| 3.51 | 35 | 1.919 | 2 |
| 3.34 | 10 diffuse | 1.886 | 1 |
| 3.26 | 18 diffuse | 1.870 | 1 |
| 3.07 | 25 | 1.836 | 1 |
| 2.95 | 22 | 1.812 | 1 |
| 2.87 | 5 | 1.776 | 1 |
| 2.81 | 10 | 1.748 | 1 |

The new salt according to the invention has also been characterised by its infrared spectrum. The infrared spectrum of the product of the following Example 2 in Nujol was obtained and this is shown in the Figure of the accompanying drawing.

The crystalline bishydrochloride of the present invention may be used in the preparation of a crystalline pentahydrate of the compound of formula I by addition of an organic or inorganic base to an aqueous solution of the bishydrochloride to a pH of 3.3 to 4.0, preferably about 3.7. The resulting pentahydrate has also been found to have a well-defined crystalline structure. This pentahydrate has been found to be remarkably stable even when stored at a temperature of 50° C. for an extended period. The pentahydrate exhibits the antibiotic properties of the above-mentioned compound (I) and finds utility as an antibiotic in like manner.

The following Examples serve to illustrate the preparation of the bishydrochloride according to the invention. All temperatures are in °C.

Proton magnetic resonance (p.m.r.) spectra were determined at 100 MHz. The integrals are in agreement with the assignments, coupling constants, J, are in Hz, the signs not being determined: s=singlet, t=triplet, d=doublet, dd=double doublet, m=multiplet and ABq=AB quartet. All the following Examples illustrate the preparation of (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate bishydrochloride.

EXAMPLE 1

Formic acid (84 ml) was added with stirring to (6R,7R)-7-[(Z)-2-(2-tritylaminothiazol-4-yl)-2-(2-t-butoxycarbonylprop-2-oxyimino)acetamido]-3-(1-pyridiniummethyl)ceph-3-em-4-carboxylate N,N-dimethylformamide solvate (41.8 g), water cooling being employed to maintain the temperature below 28°. The resulting solution was cooled to 20°, and concentrated hydrochloric acid (17.0 ml) added with stirring over 5 minutes. The mixture was stirred for 3 hours at room temperature, then filtered to remove triphenylmethanol. The filtrate was added to stirred acetone (800 ml). The triphenylmethanol was washed with formic acid (3×7 ml), and the combined washings were added to the filtrateacetone mixture. The resulting suspension was stirred for 1.25 hours, then filtered. The crystalline solid was washed with acetone and dried in vacuo to give the title compound (20.2 g), τ(D₂O) 0.95 (d, J6 Hz, pyridinium 2- and 6-H), 1.29 (dd, J6 Hz, pyridinium 4-H), 1.80 (dd, J6 Hz, pyridinium 3- and 5-H), 2.77 (s, thiazole 5-H), 4.02 (d, J5 Hz, 7-H), 4.10 and 4.47 (ABq, J16 Hz, 3-CH₂), 4.59 (d, J5 Hz, 6-H), 6.17 and 6.54 (ABq, J18 Hz, 2-H₂) and 8.36 (s, C(CH₃)₂); Chlorine found: 11.0%; calculated for $C_{22}H_{24}N_6O_7S_2Cl_2$: 11.5%; $\lambda_{max}$ (pH 6 phosphate buffer) 257 nm ($E_{1\ cm}^{1\%}$ 150).

EXAMPLE 2

(6R,7R)-7-[(Z)-2-(2-t-Butoxycarbonylprop-2-oxyimino)-2-(2-tritylaminothiazol-4-yl)acetamido]-3-(1-pyridiniummethyl)ceph-3-em-4-carboxylate N,N-dimethylformamide solvate (5 g) was added to stirred formic acid (10 ml). When the solution had cleared, concentrated hydrochoric acid (2.1 ml) was added dropwise over 2 minutes and the resultant suspension stirred at ambient temperature for a further 3 hours. The suspension was filtered and the filter bed washed with several small washes of formic acid (totalling 2.5 ml).

The filtrate was poured into industrial methylated spirit (100 ml) and then the solvent evaporated in vacuo on a rotary evaporator (water pump vacuum, bath temperature 40°) to give and oil. Ethyl acetate (50 ml) was added and evaporation continued. This process was repeated with further ethyl acetate (2×50 ml) till a foam resulted. The foam was taken up in industrial methylated spirit (100 ml) and evaporation continued carefully till signs of crystallisation were observed. The cloudy solution was refrigerated overnight and the white solid isolated by filtration and dried at 40° in vacuo to afford the title compound (150 mg).

Further careful evaporation of the liquors gave a second small crop of the title compound (150 mg). The residual industrial methylated spirit liquors were blown with a stream of nitrogen and a copious crop of crystalline material separated. This was isolated by filtration and dried in vacuo at 40° to afford the title compound (1.6 g). $\lambda_{max}$ (pH 6 phosphate buffer) 257 nm ($E_{1\ cm}^{1\%}$ 348), and $\lambda_{inf}$ 243 nm ($E_{1\ cm}^{1\%}$ 316) and $\lambda_{inf}$ 290 nm ($E_{1\ cm}^{1\%}$ 152); pmr resembled that in Example 1, chlorine assay 11.3%, water by Karl Fischer 3.0%. Debye-Scherrer powder diffraction x-ray photographs showed the material to be crystalline.

EXAMPLE 3

Crystalline solid title compound (0.5 g), prepared as in Example 1 above, was dissolved in methanol (5 ml), n-propanol (15 ml) was added, and the solution treated with diisopropyl ether (20 ml) over 20 minutes. The suspension was warmed to 50° and stirred at ambient temperature for 30 minutes. The suspension was filtered and washed to give the recrystallised title compound. (0.48 g). $\lambda_{max}$ (pH 6 phosphate) 257 ($E_{1\ cm}^{1\%}$ 349, $\epsilon$21,660) and $\lambda_{inf}$ at 245 ($E_{1\ cm}^{1\%}$ 321, $\epsilon$19,920) and 285 ($E_{1\ cm}^{1\%}$ 170, $\epsilon$10,550); $\tau$($D_2O$) identical to that of Example 1; impurities by high pressure liquid chromatography 1.2%, water content by Karl Fischer method 4.0%; chlorine, found: 10.6% ($C_{22}H_{24}N_6O_7S_2Cl_2$ 1.4$H_2O$, requires 10.9%.

PHARMACEUTICAL FORMULATIONS

The crystalline bishydrochloride of the present invention exhibits the antibiotic properties of the above-mentioned compound (I) and may be used for treating a variety of diseases caused by pathogenic bacteria in human beings and animals, such as respiratory tract infections and urinary tract infections.

In another aspect, the present invention provides pharmaceutical compositions containing the new bishydrochloride adapted for use in human or veterinary medicine. Such compositions may be presented in conventional manner with the aid of any necessary pharmaceutical carriers or excipients.

The antibiotic bishydrochloride compound according to the invention may be formulated for injection and may be presented in unit dose form in ampoules, or in multidose containers if necessary with an added preservative.

The compositions may also take such forms as suspensions, solutions or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

Desirably, such powder formulations may contain an appropriate non-toxic base in order to improve the water-solubility of the active ingredient and/or to ensure that when the powder is constituted with water, the pH of the resulting aqueous formulation is physiologically acceptable. Alternatively, the base may be present in the water with which the powder is constituted. The base may be, for example, an inorganic base such as sodium carbonate, sodium bicarbonate or sodium acetate, or an organic base such as lysine or lysine acetate.

The antibiotic compound may also be formulated as suppositories e.g. containing conventional suppository bases such as cocoa butter or other glycerides.

For medication of the eyes or ears, the preparations may be formulated as individual capsules, in liquid or semi-liquid form, or drops.

Compositions for veterinary medicine may also, for example, be formulated as intramammary preparations in either long acting or quick-release bases.

The compositions may contain from 0.1% upwards, e.g. 0.1–99%, of the active material, depending on the method of administration. When the compositions comprise dosage units, each unit will preferably contain 50–1500 mg of the active ingredient. The dosage as employed for adult human treatment will preferably range from 500 to 6000 mg per day, depending on the route and frequency of administration. For example, in adult human treatment 1000 to 3000 mg per day administered intravenously or intramuscularly should normally suffice. In treating Pseudomonas infections higher daily doses may be required.

The antibiotic compound according to the invention may be administered in combination with other therapeutic agents such as antibiotics, for example penicillins or other cephalosporins.

I claim:

1. ((6R,7R)-7-[(Z)-2-(2-Aminothiazol-4-yl)-2-(2-carboxyprop-2-oxyimino)acetamido]-3-(1-pyridiniummethyl)ceph-3-em-4-carboxylate in the form of a crystalline bishydrochloride which substantially exhibits the following 'd' values and relative intensities when subjected to Debye Scherrer powder X-ray diffraction using CoKα radiation: 'd' value Relative intensity 'd' value Relative intensity

| (Å) | $\left(\frac{I}{I_{100}}\right)$ | (Å) | $\left(\frac{I}{I_{100}}\right)$ |
|---|---|---|---|
| 10.6 | 93 | 2.76 | 12 |
| 7.9 | 22 | 2.73 | 10 |
| 6.6 | 30 | 2.65 | 15 |
| 6.4 | 10 | 2.59 | 5 |
| 5.65 | 45 | 2.53 | 3 |
| 5.43 | 15 | 2.48 | 7 |
| 5.07 | 10 | 2.43 | 10 |
| 4.90 | 10 | 2.39 | trace |
| 4.70 | 12 | 2.35 | 7 |
| 4.54 | 10 | 2.26 | 10 |
| 4.25 | 100 | 2.24 | trace |
| 4.12 | 30 | 2.19 | 4 |
| 3.97 | 30 diffuse | 2.11 | 2 |
| 3.89 | 65 | 2.09 | 4 |
| 3.82 | 25 | 2.06 | 2 |
| 3.75 | 35 | 2.03 | 2 |
| 3.60 | 35 | 1.963 | 2 |
| 3.51 | 35 | 1.919 | 2 |
| 3.34 | 10 diffuse | 1.886 | 1 |
| 3.26 | 18 diffuse | 1.870 | 1 |
| 3.07 | 25 | 1.836 | 1 |
| 2.95 | 22 | 1.812 | 1 |
| 2.87 | 5 | 1.776 | 1 |
| 2.81 | 10 | 1.748 | 1. |

* * * * *